United States Patent [19]

Swierczek

[11] Patent Number: 5,054,499
[45] Date of Patent: Oct. 8, 1991

[54] DISPOSABLE SKIN PERFORATOR AND BLOOD TESTING DEVICE

[76] Inventor: Remi D. Swierczek, 6399 Ledge Lake Ct., Concord, Ohio 44077

[21] Appl. No.: 566,160

[22] Filed: Aug. 10, 1990

Related U.S. Application Data

[63] Continuation-in-part of Ser. No. 328,907, Mar. 27, 1989, abandoned.

[51] Int. Cl.⁵ .............................................. A61B 5/00
[52] U.S. Cl. .................................. 128/770; 128/667; 606/182; 606/185
[58] Field of Search ............... 128/770, 762, 767, 637, 128/743; 604/22; 606/167, 222, 223, 224, 227, 182, 185; 206/367, 365, 339, 571

[56] References Cited

U.S. PATENT DOCUMENTS 2,974,787  3/1961  Cooper ............................... 206/63.2
3,741,197  6/1973  Sanz et al. ............................ 606/182
4,637,403  1/1987  Garcia et al. ........................ 606/182

FOREIGN PATENT DOCUMENTS 2001965   9/1970   Fed. Rep. of Germany .
3515420  10/1986   Fed. Rep. of Germany ...... 128/770
8504089   9/1985   PCT Int'l Appl. ................. 128/767
8809149  12/1988   PCT Int'l Appl. ................. 128/743

Primary Examiner—Stephen C. Pellegrino
Assistant Examiner—Robin R. Longo
Attorney, Agent, or Firm—Oldham & Oldham Co.

[57] ABSTRACT

A device that pierces the skin due to the collapsing of dome between the fingertips. Immediately after a puncture is made, a blood or exudate sample can be collected on an absorbent test strip laminated on the pressure plate. Flow enhancement of blood or exudate from the puncture site is achieved by maintenance of pressure around the site and on the imparting of a vacuum within the device.

22 Claims, 1 Drawing Sheet

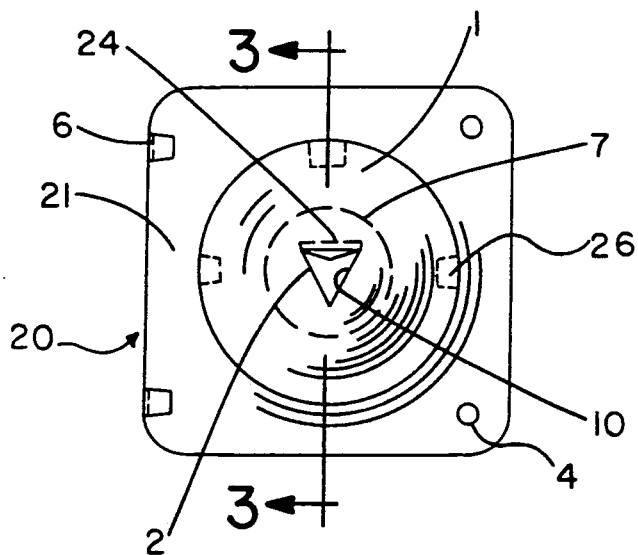
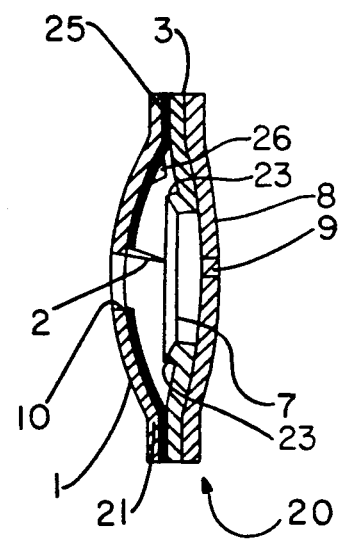
FIG.-1
FIG.-3
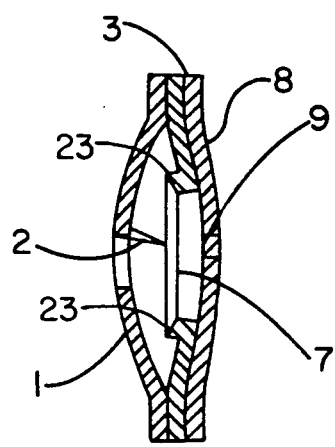
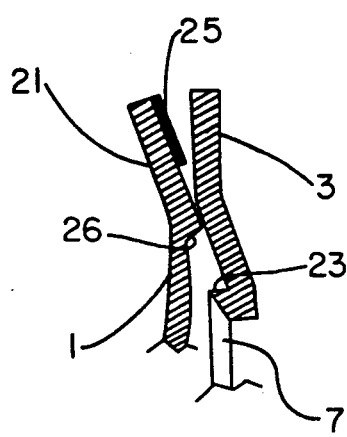
FIG.-2
FIG.-4

DISPOSABLE SKIN PERFORATOR AND BLOOD TESTING DEVICE

This is a continuation-in-part of application Ser. No. 07/328,907, filed Mar. 27, 1989, abandoned.

TECHNICAL FIELD

This invention, generally, relates to a device for drawing a small amount of blood from a person's fingertip More specifically, the invention relates to a device for obtaining a minute volume of blood and applying the same to a test medium for subsequent analysis.

BACKGROUND OF THE INVENTION

Blood testing is a common practice. The samples can be derived by merely pricking the fingertip with a sharp tool. Then, the samples must be exposed to proper test medium to acquire the test result.

In the past, a complex, sudden release, pen type device with disposable blades were used to perforate the skin painlessly. Once the skin was cut, separate test medium was introduced to the blood sample.

SUMMARY OF THE INVENTION

In accordance with the embodiments of the present invention, this device is a disposable skin perforator for obtaining a sample of blood by puncturing the skin. A further embodiment discloses a test medium attached to a pressure plate on the device which can absorb blood flowing from the puncture.

Therefore, one objective of my invention is to provide a simple, painless and inexpensive fingertip perforator that draws a sample of blood for testing and self-analysis.

Another objective of my invention is to provide a convenient holding means for litmus paper and other type test medium in such a way to allow for saturation of the test medium with blood while it is drawn.

A third objective of my invention is to provide a package that consists of a chart and bandage. The chart can be color coded to read the test results while the bandage can be used to protect the cut finger.

Other objectives of my invention will become clear with reference to the accompanying figures.

BRIEF DESCRIPTION OF THE DRAWINGS

FIG. 1 is a plan view of the perforator device.

FIG. 2 is a cross-sectional view taken on line 2—2 of FIG. 1.

FIG. 3 is a cross-sectional view similar to FIG. 2 further illustrating a sealing means and a step formed on the surface of pressure plate.

FIG. 4 is a cutaway cross-sectional view illustrating the dome in a depressed position and a step causing the formation of a means for air exchange.

DETAILED DESCRIPTION OF THE PREFERRED EMBODIMENT

Now with reference to the invention illustrated in the drawings, and looking particularly at FIG. 1, this figure shows a top plan view of the perforator device 20. Perforator device 20 comprises generally a cover plate 21 and a pressure plate 3 of essentially similar size and shape positioned adjacent to one another and attached by a plurality of welds 4 and/or crimps 6.

Cover plate 21 has a spherical shaped dome 1 formed therein so as to define a convex surface with respect to said cover plate 21 and directed outward and away from said pressure plate 3. Cover plate 21 with spherical dome 1 formed integrally therein is made of a resilient plastic or thin metal material having a substantial memory so that as dome 1 is deflected inward by a force it will return to essentially its original shape upon the removal of said force.

Pressure plate 3 is to have a rigid structure as compared to dome 1 and may be made from any plastic or metal material capable of maintaining such rigidity. Welds 4 or crimps 6 of varying number and size are contemplated. Pressure plate 3 has an aperture 7 formed generally in the center of said pressure plate 3 and having sufficient diameter to allow the passage of a barb 2 through the aperture 7. Shelf 23 defines the periphery of said aperture 7.

A barb 2 is formed in a portion of dome 1 utilizing stamping methods which are well known in the art. Barb 2 remains integral with dome 1 along edge 24 of barb 2. Barb 2 is disclosed as being essentially triangular in shape however, any shape which yields a point capable of piercing the human skin is contemplated. The stamping of dome 1 to form barb 2 results in an aperture having essentially the same dimensions as said barb 2. Barb 2 is formed so as to be directed inward and toward the aperture 7 of plate 3. After stamping, barb 2 can be coined or shaved to yield sharp yet smooth edges, by any means which are well known in the art. Alternatively, such edges of barb 2 can be achieved by grinding the same, but grinding currently appears not to be cost effective method as related to this application.

Dome 1 serves as a stress accumulating means wherein said dome 1 offers increasing resistance to applied pressure, directed inward, until said dome is deformed to an extend where it starts to undergo an inversion. At this point, resistance to the applied pressure decreases rapidly such that the central region of dome 1 containing the barb is accelerated inward and toward aperture 7 of pressure plate 3.

An alternative embodiment is contemplated wherein said cover plate 21 and said pressure plate 3 are made from a single piece of material. Cover plate 21 and pressure plate 3 are folded against each other so as to share a common edge, the outer edges of each plate being secured to one another utilizing welds 4 or crimps 6 as discussed previously herein.

The present device 20 is designed to perforate the skin on the finger of the patient. The finger should be prepared so as to cleanse and remove as many contaminates from the perforation site as is possible using techniques which are well known in the art and are not relevant to the discussion herein.

The device 20 is operated by positioning said device 20 against the patient's finger to be punctured so that the intended puncture site of the finger comes within a area defined by the outer circumference of aperture 7 in pressure plate 3. Pressure is then applied to the dome by the patient or person assisting the same. The initial applied pressure causes pressure plate 3 to be pressed against the skin of the patient further isolating the intended puncture site. As additional pressure is applied to dome 1 the stress accumulation in the dome will result in the sudden inward collapsing of dome 1, directing barb 2 through aperture 7, thereby causing a piercing of the patients skin. This inward movement of barb 2 is stopped as the inner surface of dome 1 strikes shelf 23 of pressure plate 3 to provide a predictable puncture depth.

As the applied pressure on dome 1 and pressure plate 3 is removed or reduced, the collapsed dome will resiliently return to its original shape and accordingly withdraw barb 2 from the patient's finger. The maintenance of a small amount of pressure against pressure plate 3, but pressure insufficient to cause collapse of dome 1, will create a tension to the area around the puncture site, resulting in an enhanced and continuous blood flow from the puncture site. This applied tension has a twofold effect with respect to enhanced blood flow. First, this tension maintains the skin in a stretched posture which holds edges of the puncture site apart. Second, the pressure applied to the region surrounding the puncture site forces blood out of this tissue and into adjacent tissue which may be outside or inside of this ring of applied pressure. The blood directed inward seeks relief from this pressure and as a result exits through the puncture site. Flow enhancement of the blood from the puncture site is also increased by the creation of a partial vacuum or pressure differential within the confined area defined by dome 1, pressure plate 3 and the patient's finger. This area as defined while the dome is in the collapsed position, has a comparatively reduced volume compared to the same area with dome 1 in its original position. While in the depressed position, the person administrating the applied force may simply cover or obstruct aperture 10 formed from the stamping of barb 2, as the pressure is withdrawn. This sudden increase in volume in the area enclosed by the pressure plate 3 and dome 1 creates a vacuum at the aperture 7. The vacuum causing free flow of blood from the puncture site.

After the barb has been withdrawn from the finger, the disposable skin perforator can be removed and a blood sample collected as in prior art devices by squeezing the finger, if necessary.

To further effect a vacuum in the confined area of perforator device 20, a seal or gasket 25 can be placed between the cover plate 21 and the pressure plate 3 as is shown in FIG. 3. This seal or gasket 25 can be made from a variety of flexible plastic or rubber materials as is well known in the art and serves to prevent air passage into and out of the confined area of perforator device 20 through the contact between the peripheral edges of cover plate 21 and peripheral plate 3. A preferred manner of creating a seal or gasket 25 is to apply a laminate to the inner surface of either the cover plate 21 or the pressure plate 3. Such laminate becomes sandwiched between cover plate 21 and pressure plate 3 during the application of welds 4 or crimps 6.

Still another embodiment which is contemplated to create a vacuum for improving flow enhancement is a formation of one or more steps 26 in pressure plate 3. These steps 26 are essentially projections of varying width formed on the inner surface of pressure plate 3 or cover plate 21 along its periphery and located between the crimper 6 or welds 4. Steps 26 are of sufficient size so as to extend into the area defined by and below the dome 1. Steps 26 do not interfere with the depression of the dome but contact the opposing surface after substantial depression of the dome. As dome 1 is depressed to effectuate a puncture, steps 26 cause sufficient deflection along the periphery of cover plate 21 to form a temporary break in the seal between cover plate 21 and pressure plate 3 as shown in FIG. 4. This break allows for the exit of air trapped within the confined area of the perforator device 20. Following puncture of the finger by barb 2, and the gradual withdrawal of the applied pressure from dome 1, the seal 25 is reformed thereby creating the vacuum to enhance blood flow from the puncture site.

The present invention, in a further preferred embodiment, comprises an absorbent test strip 8 and is best illustrated in the cross-sectional views of FIGS. 2 and 3. Test strip 8 is disclosed as generally a pad or sheet of material capable of absorbing blood or exudate from the puncture site created by barb 2. The test strip 8 is contemplated as being treated or coated with various reagents which react with the blood or exudate to cause color or chemical changes which then can be quantitatively or qualitatively compared to a known standard. Most home use test strips utilize color change techniques and yield fairly quick results which can be interpreted by comparing the test strip to a color coded chart provided with the device. The most common test strip contemplated is that used for the determination of the patient's blood sugar level. The technology of such test strips is well known in the art.

Test strip 8 is disclosed as being laminated to the outer surface of pressure plate 3. Lamination may be done using known adhesives or by means of crimps 6. Test strip 8 may be of varying shapes or sizes but preferably has a length slightly greater than the diameter of aperture 7. Although, not required, test strip 8 contains a aperture dimensioned and positioned to allow passage of barb 2 therethrough. In this embodiment the device is used similar to that as described previously herein. However, test strip 8 is positioned immediately adjacent to the patient's finger with the aperture 9 in the test strip 8 identifying the intended test site.

Following the puncture of the patient's finger by barb 2, the disposable skin perforator 20 remains in contact with the finger to allow the blood or exudate from the puncture site to be absorbed onto test strip 8. Maintenance of a pressure pressing pressure plate 3 against the finger, but which is insufficient to cause collapse of dome 1, will enhance blood flow as previously described and allow for saturation of test strip 8 with the blood or exudate from the puncture site.

This device, incorporating test strip 8 places the test medium immediately adjacent to the puncture site and allows blood collection and testing to begin immediately upon puncture. Furthermore, test strips 8 representing various thickness may be used. Such strips 8 can extend into the recession found in the bottom surface of pressure plate 3 by shelf 23. In a less preferred, but contemplated embodiment, test strip 8 would omit the formation of aperture 9 therein. Barb 2 is of sufficient length and sharpness to cut test strip 8 simultaneously with the skin of the fingertip. However, it is thought that such a practice may permit the introduction of fibrous material from test strip 8 into the puncture site formed by barb 2.

Hence the foregoing embodiments are designed to be simple in construction, economical to manufacture and capable of being packaged under sterile conditions. The various embodiments of the present invention are contemplated as being either disposable or reusable following sterilization using known techniques. While in accordance with the patent statutes the best mode and preferred embodiment of the invention have been described, it is to be understood that the invention is not limited thereto, but is rather to be measured by the scope and the spirit of the appended claims.

What is claimed is:

1. A skin perforator for obtaining a sample of blood by puncturing the skin comprising:
   (a) a pressure plate containing an aperture formed therein wherein said pressure plate is placed adjacent to the area of skin to be punctured;
   (b) a cover plate having a resilient convex panel formed therein, said cover plate being attached to said pressure plate and said convex panel having a point penetrating barb formed integrally therefrom and directed inward toward said aperture in said pressure plate wherein a pressure applied to the convex panel and directed toward said pressure plate overcomes the resistance of said convex panel and said convex panel undergoes at least a partial inversion to cause said barb to suddenly and rapidly penetrate the skin causing a puncture, said convex panel having a memory so as to resiliently return to its original convex shape upon removal of said pressure thereby withdrawing the barb from the skin.

2. The skin perforator as recited in claim 1 wherein said perforator further comprises a means for effecting at least a partial vacuum around said puncture during withdrawal of the barb from the skin.

3. The skin perforator as recited in claim 2 wherein said perforator further comprises a sealing means around at least a substantial portion of a periphery of said pressure plate and said cover plate.

4. The skin perforator as recited in claim 2 wherein said perforator further comprises at least one step formed along a periphery between said pressure plate and said cover plate.

5. The disposable skin perforator as recited in claim 4 wherein at least one step formed along a periphery between said pressure plate and said cover plate extends inwardly to a region such that said step contacts said convex panel upon said convex panel's collapse.

6. The skin perforator as recited in claim 1 wherein said perforator further comprises a means for controlling the penetration depth of said skin by said barb.

7. The skin perforator as recited in claim 6 wherein said penetration controlling means comprises a shelf formed around said aperture in said pressure plate.

8. The skin perforator as recited in claim 1 wherein said perforator further comprises an absorbent test strip attached to said pressure plate to absorb blood or exudate flowing from a puncture site formed by the penetration of said barb.

9. The skin perforator as recited in claim 8 wherein said test strip is treated with at least one reagent for medical analysis.

10. The skin perforator as recited in claim 8 wherein said test strip further comprises an aperture therein and positioned to allow passage of at least a portion of said barb.

11. A skin perforator for obtaining and collecting a sample of blood by puncturing the skin comprising:
   a pressure plate containing an aperture wherein said pressure plate is placed adjacent to the area of skin to be punctured;
   an absorbent test strip attached to said pressure plate to absorb blood or exudate flowing from a puncture site formed by the penetration of a barb;
   a cover plate having a resilient convex panel formed therein, said cover plate being attached to said pressure plate and said convex panel having a point penetrating barb formed integrally therefrom and directed inward toward said aperture in said pressure plate wherein a pressure applied to the convex panel and directed toward said pressure plate overcomes the resistance of said convex panel and said convex panel undergoes at least a partial inversion to cause said barb to suddenly and rapidly penetrate the skin causing a puncture, said convex panel having a memory so as to resistantly return to its original convex shape upon removal of said pressure thereby withdrawing the barb from the skin.

12. The skin perforator as recited in claim 11 wherein said perforator further comprises a means for effecting at least a partial vacuum during withdraw of the barb from the skin.

13. The skin perforator as recited in claim 12 wherein said perforator further comprises a sealing means around at least a periphery between said pressure plate and said cover plate.

14. The skin perforator as recited in claim 12 wherein said perforator further comprises at least one strip formed along a periphery between said pressure plate and said cover plate.

15. The skin perforator as recited in claim 14 wherein at least one step formed along a periphery between said pressure plate and said cover plate extends inwardly to a region such that said step contacts said convex panel upon said convex panels collapse.

16. A skin perforator as recited in claim 11 wherein said perforator further comprises a means for controlling the penetration depth of said skin by said barb.

17. The skin perforator as recited in claim 16 wherein said penetration controlling means comprises a shelf formed around said aperture in said pressure plate.

18. The skin perforator as recited in claim 11 wherein said strip is treated with at least on reagent for medical analysis.

19. The skin perforator as recited in claim 11 wherein said test strip further comprises an aperture formed therein and positioned to allow passage of a least a portion of said barb.

20. The skin perforator as recited in claim 11 wherein said aperture is sized to enhance blood blow from the puncture when slight pressure is maintained upon said pressure plate.

21. A method for puncturing the skin and collecting a blood sample comprising:
   (a) isolating an area of skin to be punctured;
   (b) placing a skin perforator device adjacent to the area to be punctured, said skin perforator device comprising a pressure plate containing an aperture surrounding the area of skin to be punctured, an absorbent test strip attached to said pressure plate to absorb blood or exudate flowing from a puncture site formed by the penetration of a barb, a cover plate having resilient convex panel formed therein, said cover plate being attached to said pressure plate and said convex panel having a point penetrating barb formed integrally therefrom and directed inward toward said aperture in said pressure plate;
   (c) applying a pressure to overcome the resistance of said convex panel and to cause at least a partial inversion of said convex panel and a rapid and sudden penetration of the skin by said barb;
   (d) reducing said pressure such that said convex panel resiliently returns to its original convex shape thereby withdrawing the barb from said skin;
   (e) maintaining a pressure upon said skin perforator to enhance blood flow from the puncture and obtain essentially immediate collection of blood or exudate by said test strip.

22. The method according to claim 21, comprising a further step, inserted following step c: effecting at least a partial vacuum to the area immediately adjacent to the puncture site to enhance blood flow from the puncture site.

* * * * *